(12) United States Patent
Aburatani et al.

(10) Patent No.: US 7,794,982 B2
(45) Date of Patent: Sep. 14, 2010

(54) METHOD FOR IDENTIFYING GENE WITH VARYING EXPRESSION LEVELS

(75) Inventors: Hiroyuki Aburatani, Tokyo (JP); Shumpei Ishikawa, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 11/721,737

(22) PCT Filed: Dec. 15, 2005

(86) PCT No.: PCT/JP2005/023439

§ 371 (c)(1),
(2), (4) Date: Jun. 14, 2007

(87) PCT Pub. No.: WO2006/064964

PCT Pub. Date: Jun. 22, 2006

(65) Prior Publication Data

US 2008/0138807 A1    Jun. 12, 2008

(30) Foreign Application Priority Data

Dec. 17, 2004    (JP) .............................. 2004-366671

(51) Int. Cl.
*C12Q 1/68*    (2006.01)
*C12P 19/34*    (2006.01)

(52) U.S. Cl. .................... 435/91.2; 435/6; 435/91.1

(58) Field of Classification Search ................ None
See application file for complete search history.

(56) References Cited

U.S. PATENT DOCUMENTS

| | | | | |
|---|---|---|---|---|
| 6,368,799 B1 * | 4/2002 | Chee | ............................. | 435/6 |
| 7,402,386 B2 * | 7/2008 | Kurn et al. | ..................... | 435/6 |
| 2002/0048749 A1 * | 4/2002 | Lipshutz et al. | ................ | 435/6 |

FOREIGN PATENT DOCUMENTS

WO    WO 2004/101806 A2    11/2004

OTHER PUBLICATIONS

Wang et al., "Whole Genome Amplification and High-Throughput Allelotyping Identified Five Distinct Deletion Regions on Chromosomes 5 and 6 in Microdissected Early-Stage Ovarian Tumors," Cancer Research, May 2001, vol. 61, pp. 4169-4174.*
Hirota et al., "Allelic Expression imbalance of the Human CYP3A4 gene and individual phenotypic Status," Human Mol. Gen., first published Sep. 2004, vol. 13, pp. 2959-2969.*
Berthet et al., "Phi29 polymerase based random amplification of viral RNA as an alternative to random RT-PCR," BMC Molecular Biology, 2008, vol. 9, No. 77, pp. 1-7.*
J.M. Lage et al., "Whole genome analysis of genetic alterations in small DNA samples using hyperbranched strand displacement amplification and array-GCH", Genome Res. 2003, vol. 13, No. 2, pp. 294-307.
H.S. Lo et al., "Allelic variation in gene expression is common in the human genome", Genome Res. 2003, vol. 13, No. 8, pp. 1855-1862.
Julian C. Knight, "Allele-specific gene expression uncovered", Trends in Genetics, vol. 20, No. 3, Mar. 2004, pp. 113-116.
Gang Wang et al., "DNA amplification method tolerant to sample degradation", Genome Research, Cold Spring Harbor laboratory press, Woodbury, NY, US, vol. 14, Jan. 1, 2004, pp. 2357-2366.
Tomi Pastinen et al., "Cis-Acting Regulatory Variation in the Human Genome", Science, vol. 306, Oct. 22, 2004, pp. 647-649.
Tomi Pastinen et al., "A Survey of Genetic and Epigenetic variation affecting Human Gene Expression", Physiol. Genomics 16: 184-193, 2003.
Mei Guo et al., "Allelic Variation of Gene Expression in Maize Hybrids", The Plant Cell, vol. 16, 1707-1716, Jul. 2004.
EP Search Report 05 81 9860, dated Sep. 2008.
Rebecca Pask et al., "Investigating the utility of combining Φ29 whole genome amplification and highly multiplexed single nucleotide polymorphism BeadArray™ genotyping", BMC Biotechnology 2004, 4:15, pp. 1-8.
EP Office Action Application No. 05 819 860.7-2402 dated Apr. 1, 2010.
GenomiPhi DNA Amplification Kit Amersham (2003) pp. 1-4.
Rohini Dhulipala et al., Transcriptome 2002: From Functional Genomics to Systems Biology, Mar. 10-13, 2002 (abstract).

* cited by examiner

*Primary Examiner*—Young J Kim
(74) *Attorney, Agent, or Firm*—Stephen A. Bent; Foley & Lardner LLP

(57) ABSTRACT

This invention relates to a method for searching for a genetic polymorphism for identifying a gene whose expression level is different between alleles and to a method for searching for a phenotype-associated genetic polymorphism. More particularly, the invention relates to a method for effectively identifying a gene whose expression level is different between alleles by utilizing a genetic polymorphism present in intranuclear RNA.

7 Claims, 8 Drawing Sheets

```
SEQUENCE LISTING

<160> NUMBER OF SEQ ID NOS: 3

<210> SEQ ID NO 1
<211> LENGTH: 15
<212> TYPE: DNA
<213> ORGANISM: Homo sapiens
<220> FEATURE:
<221> NAME/KEY: misc_feature
<223> OTHER INFORMATION: partial sequence of human peroxisome
      proliferator-activated receptor gamma

<400> SEQUENCE: 1
ttccagatta cactc                                                    15

<210> SEQ ID NO 2
<211> LENGTH: 15
<212> TYPE: DNA
<213> ORGANISM: Homo sapiens
<220> FEATURE:
<221> NAME/KEY: misc_feature
<223> OTHER INFORMATION: partial sequence of human peroxisome
      proliferator-activated receptor gamma

<400> SEQUENCE: 2
ttccatatta cactc                                                    15

<210> SEQ ID NO 3
<211> LENGTH: 15
<212> TYPE: DNA
<213> ORGANISM: Homo sapiens
<220> FEATURE:
<221> NAME/KEY: misc_feature
<223> OTHER INFORMATION: partial sequence of human peroxisome
      proliferator-activated receptor gamma
<220> FEATURE:
<221> NAME/KEY: modified_base
<222> LOCATION: (6)..(6)
<223> OTHER INFORMATION: G or T

<400> SEQUENCE: 3
ttccanatta cactc                                                    15
```

METHOD FOR IDENTIFYING GENE WITH VARYING EXPRESSION LEVELS

TECHNICAL FIELD

The present invention relates to a method for searching for a gene polymorphism for identifying a gene whose expression level is different between alleles, and to a method for searching for a phenotype-associated gene polymorphism.

BACKGROUND ART

Genes on the same genomic position but on the different alleles can be different in expression level. This phenomenon is a relatively new concept that has been reported recently (Knight J C. Allele-specific gene expression uncovered, Trends Genet. March; 20(3): 113-6. PMID: 15049300, 2004).

Genes expressed differentially between alleles are roughly classified into two types: imprinted gene and non-imprinted gene. In the phenomenon of the former, i.e. the imprinted gene, when one allele is inherited from one of the parents while the other allele from the other parent, one of the alleles is physiologically inactivated (e.g., methylated), whereby the expression of the gene is inhibited in cells or tissues. Also for the latter (i.e. non-imprinted genes), there are some cases where a difference in expression level is observed between alleles. With respect to such a difference, it is thought that a genomic polymorphism in a gene or a region adjacent thereto between alleles serves as a cis-acting element for regulating the expression of a gene in the vicinity of the polymorphism, thereby leading to a difference in gene expression level between alleles. Variations in expression of each allele resulting from different genomic DNA sequences are considered to be properties that are inherited over generations, and such properties may influence differences in gene expression levels among individuals and differences in body constitutions, pathological conditions and risks thereof, and responsiveness to drugs, among individuals.

Difference in gene expression levels between alleles can be most accurately assayed within a same cell, or under identical environmental conditions. In assaying a difference in gene expression levels between alleles, it is important from which allele a certain RNA is derived can be determined. To this end, the presence of a polymorphism that enables distinction of alleles (e.g., SNP) is required in an RNA sequence, which is a transcript of a gene, and the polymorphism in the RNA sequence is measured to determine a difference in gene expression level between alleles. There are several reports on determining a difference in gene expression level between alleles using such a polymorphism (SNP) on RNA (Cowles C R, Hirschhorn J N, Altshuler D, Lander E S, Detection of regulatory variation in mouse genes, Nat Genet. November; 32(3): 432-7, PMID, 12410233, 2002; Yan H, Yuan W, Velculescu V E, Vogelstein B, Kinzler K W, Related Allelic variation in human gene expression, Science. August 16; 297 (5584): 1143, PMID, 12183620, 2002; Bray N J, Buckland P R, Owen M J, O'Donovan M C, Cis-acting variation in the expression of a high proportion of genes in human brain, Hum Genet., 2003 July; 113 (2): 149-53. Epub, May 1, PMID: 12728311, 2003).

However, the techniques employed in the reports are a combination of RT-PCR with a direct sequencing reaction or single-nucleotide extension, wherein cDNA is synthesized from mRNA and amplified, and then arbitrarily selected polymorphisms are individually subjected to typing. These techniques are not capable of simultaneously measuring many genes.

To date, extensive analysis of many genes using microarrays for SNP typing has been reported (Lo H S, Wang Z, Hu Y, Yang H H, Gere S, Buetow K H, Lee M P, Allelic variation in gene expression is common in the human genome, Genome Res. August; 13(8): 1855-62. PMID: 12902379, 2003). In this analysis, mRNA with poly(A) is converted into cDNA by the common RT method using a poly(T) primer, samples are prepared by the multiplex PCR technique using many specific primers in accordance with the same protocol as a conventional genomic DNA typing technique, and samples are hybridized to the arrays to measure the expression levels of cDNA (mRNA) that differ between alleles based on the signal ratio. However, mature mRNA with poly (A) has only exon sequences following splicing, and so such sequences are too short to comprise enough polymorphisms (SNPs) to be evaluated. Thus, because available polymorphisms (SNPs) are limited, it is difficult to find a gene whose expression level varies in every allele.

The correlation between genetic polymorphism and certain phenotype and gene expression (e.g., difference in disease or drug efficacy) has drawn attention. However, to study the correlation between certain genetic polymorphism and phenotype and gene expression, it is required to examine a huge number of SNPs for respective traits in the case of, for example, genomic SNPs (about 10 million according to the NCBI dbSNP (build 123) reported in October 2004), and thus it is indeed difficult to do so.

If genes whose phenotype and gene expression differs between alleles can be rapidly and effectively selected in order to study the correlation between the thus selected genetic polymorphism and the phenotype and gene expression, accordingly, the cause of a disease, effective therapeutic methods, or the like may be examined by the completed procedures.

DISCLOSURE OF THE INVENTION

Under the above circumstances, one object of the present invention is to provide a method for rapidly and effectively searching for a genetic polymorphism that enables identifying a gene whose expression level is different between alleles. Also, another object of the present invention is to provide a method of utilizing the genetic polymorphism searched for by the above method to search for a phenotype-associated genetic polymorphism.

We have conducted extensive studies in order to achieve the above objects. As a result, expecting that a gene whose expression level is different between alleles could be effectively discovered by utilizing a genetic polymorphism on intranuclear RNA, we selected a DNA polymerase, which is capable of selectively amplifying intranuclear RNA, in the procedures for discovering a gene of interest. As a result, we succeeded in determining a genetic polymorphism (SNP) that enables identifying a gene whose expression level is different between alleles, thereby leading to the completion of the present invention.

Specifically, the present invention includes the following characteristics.

(1) A method for searching for a genetic polymorphism for identifying a gene whose expression level is different between alleles, comprising the following steps of:
  (a) synthesizing cDNA from total RNA or intranuclear RNA by reverse transcription using a random primer;
  (b) selectively amplifying cDNA derived from long intranuclear RNA as a primary transcript using a random primer and a strand-displacing DNA polymerase that reacts at an isothermal temperature;

(c) detecting a genetic polymorphism present in the amplified cDNA;

(d) comparing the expression levels of cDNAs from the respective alleles on the genomic DNA whose genetic polymorphism is heterozygous, based on the detected polymorphism; and (e) selecting the genetic polymorphism used for comparison, where the expression levels of cDNAs from the respective alleles significantly differ from each other.

In said method, examples of the DNA polymerase usable include φ29 DNA polymerase.

Steps (c) and (d) preferably comprise labeling the amplified cDNAs, which is in turn subjected to hybridization with a genetic polymorphism-specific probe, to compare the expression levels of cDNAs from respective alleles based on the hybridization reaction.

In this method, single nucleotide polymorphism (SNP) can be used as the genetic polymorphism.

(2) A method for searching for a phenotype-associated genetic polymorphism comprising using a genetic polymorphism searched for by the above method to evaluate the correlation between the genetic polymorphism or gene expression level and the phenotype.

In this method, examples of phenotypes include pathological conditions and severity of a disease, risks of developing a disease, responsiveness to drugs, responsiveness to foods, responsiveness to chemical substances, and responsiveness to environmental factors.

(3) A method for searching for a genetic polymorphism-associated phenotype comprising using the genetic polymorphism searched for by the above method to evaluate the correlation between the genetic polymorphism or gene expression level and the phenotype.

In this method, examples of phenotypes include pathological conditions and severity of a disease, risks of developing a disease, responsiveness to drugs, responsiveness to foods, responsiveness to chemical substances, and responsiveness to environmental factors.

The present invention provides a method for rapidly and effectively searching for a genetic polymorphism that enables identifying a gene whose expression level is different between alleles. The genetic polymorphism searched for in this manner enables distinguishing of expression levels in different alleles. Accordingly, such a polymorphism can be used as an effective means for analyzing a phenotype associated with the gene of interest. Further, discovering a correlation between the genetic polymorphism searched for in the aforementioned manner and a phenotype (e.g., risk of developing a disease, or drug responsiveness) may lead to examining the cause of a disease or effective therapeutic methods.

BEST MODES FOR CARRYING OUT THE INVENTION

Figure 1:
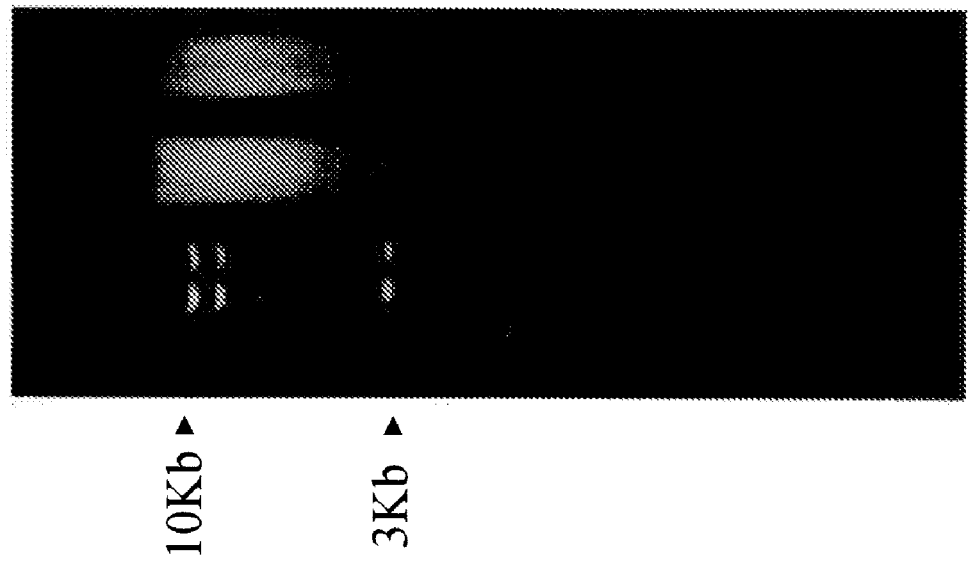
FIG. 1 is an electrophoresis showing cDNA obtained via amplification with the use of φ29 DNA polymerase.

Hereafter, the present invention is described in detail. This patent application claims priority from Japanese Patent Application No. 2004-366671 filed on Dec. 17, 2004, and includes all or part of the contents as disclosed in the description and/or drawings thereof.

1. Searching for a Genetic Polymorphism That Enables Identifying a Gene Whose Expression Level is Different Between Alleles The present invention provides a method for studying a gene with expression levels that vary between alleles. The term "a gene whose expression level is different between alleles" as used herein refers to a gene in which the expression level in one allele differs from that in the other allele. Gene expressions in the respective alleles are distinguishable from each another using specific genetic polymorphisms an indicator; however, not all genetic polymorphisms enable differences in expression levels in different alleles to be distinguished. The present invention, accordingly, provides a method for rapidly and effectively searching for a genetic polymorphism that enables determination of differences in expression levels between alleles.

(1) Synthesis of cDNA from Intranuclear RNA and Amplification Thereof

In this method, cDNA is synthesized from intranuclear RNA. The term "intranuclear RNA" as used herein refers to a primary transcript that is not spliced after transcription from genomic DNA and remains in the nucleus before transferring to the cytoplasm. Thus, many intranuclear RNAs comprise both exons and introns of the genome and have a long strand. (For example, for the 21,804 reference sequences present on the genomic sequence of the Human Genome Build 34 (http://genome.ucsc.edu/) reported in April 2004, the average length is 85,284 bp, the median is 22,855 bp, and sequences longer than 5,000 bp account for about 84% of the all sequences.)

In order to measure differences in expression levels between alleles, genetic polymorphisms must be present in RNA, which is a gene transcript. Since intranuclear RNA, not spliced, might have a long strand, we expected that intranuclear RNA might contain many genetic polymorphisms that enable a gene whose expression level is different between alleles to be distinguished. For example, while the 21,804 reference sequences present on the genomic sequence of the Human Genome Build 34 (http://genome.ucsc.edu/) reported in April 2004 have an average mRNA length of 2,757 bp and a median mRNA length of 2,316 bp, the average length of intranuclear RNA comprising introns is 85,284 bp and the median thereof is 22,855 bp. Such a long strand would enable evaluation of regions about 40 times the regions that could be evaluated in mRNA, without considering the density of genetic polymorphisms, accordingly.

To synthesize cDNA from intranuclear RNA, intranuclear RNA is selectively extracted from a sample, from which cDNA is then synthesized. Alternatively, after extraction of total RNA from a sample, cDNA is synthesized from the extracted RNA, and then only cDNA derived from longer intranuclear RNA is selectively amplified.

In one method, a nuclear fraction is first extracted from a sample. The sample is not particularly limited, provided that it is from a substance that is to be analyzed by this method for the genetic polymorphism for identifying a gene whose expression level is different between alleles. Examples of the sample that can be used include samples derived from animals, plants, and microorganisms (e.g., fungi or bacteria), commercially available cell strains, and deposited cell strains. Samples are preferably from mammalians, more preferably humans. Also, the forms of samples are not particularly limited. When the samples are from humans for example, usable samples are in the form of body fluid, such as blood, saliva, lymph, airway mucus, bone marrow fluid, urine, and coeliac fluid, cells, or tissues.

Nuclear fractions can be extracted by a method known in the art. For example, cells are broken using a homogenizer, and nuclei can be separated via differential centrifugation or density gradient centrifugation (see, for example, Molecular cloning, Chapter 17.8, Preparation of nuclear extracts from tissue/cultured mammalian cells, CSHL Press, ISBN 0-87969-577-3).

Subsequently, cDNA is synthesized from intranuclear RNA prepared in the above-described manner by reverse transcription using a random primer. Use of random primer enables synthesis of cDNA from any sequence of RNA (i.e., intranuclear RNA) in samples.

The reversely-transcribed cDNA is then amplified using a random primer. Because intranuclear RNA, not spliced, has a long strand, the RNA cannot be amplified with a DNA polymerase as commonly used for amplification. Thus, a DNA polymerase that catalyzes a strand displacement under isothermal reaction conditions is used in this method. The DNA polymerase having such properties includes, but not particularly limited to, φ29 DNA polymerase (Genomiphi™, Amersham Bioscience). The amplification reaction catalyzed by the φ29 DNA polymerase is very stable, so cDNA synthesized by reverse transcription can be directly used for the amplification reaction using φ29 DNA polymerase without the need of any purification process. Additionally, since the yield is at the order of μg, extremely small amounts of samples, such as clinical specimens, can be amplified without loss of the sample caused by purification, and thus the use of φ29 DNA polymerase is particularly preferable in the method of the present invention. Further, an alternative polymerase is Bst polymerase, which is commercially available from New England Biolabs (Lage J M, Leamon J H, Pejovic T, Hamann S, Lacey M, Dillon D, Segraves R, Vossbrinck B, Gonzalez A, Pinkel D, Albertson D G, Costa J, and Lizardi P M, Whole genome analysis of genetic alterations in small DNA samples using hyperbranched strand displacement amplification and array-CGH, Genome Res. 2003 February; 13(2): 294-307, PMID: 12566408).

The above-described DNA polymerases terminate the amplification reaction at the end of a DNA fragment during DNA amplification, so the amplification efficiency significantly lowers around the end. When a short DNA fragment is to be amplified, the amplification rate of the whole fragment lowers due to the short distance between both ends, resulting in selective amplification of a long DNA fragment, i.e., unspliced intranuclear RNA (Lage J M, Leamon J H, Pejovic T, Hamann S, Lacey M, Dillon D, Segraves R, Vossbrinck B, Gonzalez A, Pinkel D, Albertson D G, Costa J, and Lizardi P M, Whole genome analysis of genetic alterations in small DNA samples using hyperbranched strand displacement amplification and array-CGH., Genome Res., 2003 February; 13(2): 294-307, PMID: 12566408; General Amplification of Chromosomal DNA by phi29 DNA polymerase, Amersham Bioscience).

Accordingly, cDNA derived from intranuclear RNA can be selectively synthesized and amplified by preparing total RNA (including intranuclear RNA and mRNA) from samples, synthesizing cDNA from various RNA species by reverse transcription using a random primer, and amplifying the cDNA using the aforementioned DNA polymerase (e.g., φ29 DNA polymerase) that is capable of selectively amplifying a long-stranded cDNA (i.e., cDNA derived from long nuclear RNA). The method of amplifying cDNA from intranuclear RNA can omit a procedure of selectively extracting intranuclear RNA and thus is preferable in the present invention. Total RNA can be extracted by a method known in the art. For example, the guanidine/cesium method or the acid guanidium-phenol-chloroform (AGPC) method can be employed.

(2) Genetic Polymorphism and Allele Expression Level

Expression levels of a gene (an amplified cDNA) from each allele are then compared, wherein the expression levels are compared between heterozygous alleles. The term "heterozygous alleles" refers to two alleles each having genetic polymorphisms different from each other in genomic DNA. When there are heterozygous alleles, accordingly, amplified cDNA from each allele can be distinguished. When the above expression levels are significantly different, the genetic polymorphism of interest can be selected as an indicator for identifying a gene whose expression level is different between alleles.

The term "genetic polymorphism" or "polymorphism" refers to a difference in gene that causes variations in traits or morphologies among individuals, and examples thereof include a single nucleotide polymorphism (SNP), a haplotype and the like. The term "SNP" refers to a mutation of a single nucleotide in the nucleic acid of a certain gene or genes. Such SNP is known to occasionally cause variations in traits or morphologies among individuals. The term "haplotype" refers to a polymorphism represented by the type and the number of alleles in a continuous gene region or in several mutation sites in genes. The frequency of haplotype recombination is lower than that of usual recombination, and is likely to be genetically conserved. When the correlation between a polymorphism and a phenotype is to be studied, accordingly, it might be important to study the correlation with a given haplotype in addition to the correlation with respective mutations. Further, examples of genetic polymorphisms include insertion/deletion polymorphisms, polymorphisms resulting from a difference in numbers of repetition in a repeated sequence, and restriction fragment length polymorphisms. In the method of the present invention, use of a single nucleotide polymorphism (SNP) is preferable because many methods of detecting SNP are available and differences between alleles can be easily distinguished based on difference in a single nucleotide.

Genetic polymorphisms that can be employed are not particularly limited, and genetic polymorphism information can be easily obtained from public databases or the like. For example, SNP and haplotype information for humans or mice can be obtained from the NCBI database (http://www.ncbi.nlm.nih.gov/SNP/), and human SNP information can be obtained from the JSNP database (http://snp.ims.u-tokyo.ac.jp/index_ja.html). A person skilled in the art can easily obtain other genetic polymorphism information.

Detection of genetic polymorphisms and measurement of expression levels from alleles carrying genetic polymorphisms can be carried out in accordance with techniques known in the art.

For example, the detection of genetic polymorphisms and the measurement of gene expression levels from alleles can be carried out by hybridization with a probe specific for a single genetic polymorphism. A probe can be labeled with an adequate means, such as a fluorescent or radioactive substance, if needed. Any probe can be used, provided that such a probe comprises a site of genetic polymorphism and hybridizes specifically to the amplified cDNA. A specific probe design is known in the art. Any hybridization conditions can be employed, provided that genetic polymorphisms can be sufficiently distinguished. Under such conditions, a probe hybridizes in the case of a certain single genetic polymorphism but does not hybridize in the case of another genetic polymorphism. An example is stringent conditions, which are known in the art.

One end of a probe may be fixed onto a substrate and may be used as a DNA chip (microarray). In such a case, a DNA chip may comprise probes corresponding to a single genetic polymorphism fixed thereon, or probes corresponding to both of the genetic polymorphisms fixed thereon. Detection of genetic polymorphisms using such DNA chip is described in, for example, "DNA microarrays and latest PCR method," Masaaki Muramatsu and Hiroyuki Nawa (ed.), Shujunsha, 2000, chap. 10.

As a specific example of the technique for detecting genetic polymorphisms using DNA chip, a method involving the use of the GeneChip® Human Mapping 100K Array (Affymetrix) is explained. The GeneChip® Human Mapping 100K Array comprises two arrays that can detect more than 100,000 SNPs in the genome. A sample (e.g., genome or cDNA) is cleaved with a restriction enzyme (e.g., XbaI or HindIII), an adapter is attached, a single type of primer (each type for XbaI and HindIII) specific for the adapter is used to amplify the sample by PCR, and the amplified product is then labeled. Two arrays are designed to be complementary to each SNP allele, SNP of the sample is evaluated based on the signal after hybridization, and expression levels can be compared between alleles based on signal intensity or signal ratio. Concerning details of the DNA chip, reference may be made to the product information and the data sheet posted on http://www.affymetrix.cojp/products/arrays/specific/100k. and http://www.affymetrix.co.jp/pdf/Mapping_100K.pdf.

Also, genetic polymorphisms can be detected via any techniques known in the art, in addition to the aforementioned techniques. Examples of the techniques that can be employed include a method involving the use of a primer specific for a genetic polymorphism, a method involving the use of a restriction fragment length polymorphism (RFLP), direct sequencing, denaturing gradient gel electrophoresis (DGGE), a method involving the utilization of chemical cleavage of mismatch (CCM), primer extension (PEX), the invader method, quantitative real-time PCR detection (the TaqMan method), and the like.

In the method of the present invention, use of a DNA chip (or a microarray) that enables detection of as many genetic polymorphisms as possible in a simple and rapid manner is preferable.

As described above, when the gene expression level (or signal intensity) in each allele is measured based on the difference in genetic polymorphisms and the gene expression levels of between alleles significantly differ from each other, such genetic polymorphisms are selected. More specifically, the ratio of the allele exhibiting a high expression level to the allele exhibiting a low expression level is determined, and the genetic polymorphism exhibiting a ratio of at least 1.3:1, and preferably at least 1.5:1, is selected. The ratio of 1:1 means that the gene expression levels are substantially the same in both alleles.

The genetic polymorphism exhibiting different expression levels, in comparison of the expression levels of each allele with the utilization of the genetic polymorphisms, can be selected as a genetic polymorphism for identifying a gene whose expression level is different between alleles. By merely detecting the thus-selected genetic polymorphism in turn, it is possible to determine whether or not a given specimen has an allele exhibiting a high expression level. Also, a gene whose expression level is different between alleles may correlate with a phenotype as described below, and so, utilizing the thus-selected genetic polymorphism, the correlation between the genetic polymorphism and the phenotype may be elucidated.

2. Method for Searching Phenotype-Associated Genetic Polymorphism

Genetic polymorphisms are a genetic difference that causes variety in traits or morphologies among individuals. Thus, a genetic polymorphism may be correlated with a phenotype in some way or another. However, there are present numerous genetic polymorphisms, i.e., as many as at least about 10 million SNPs on genome (the NCBI dbSNP build 123 reported in October 2004), and so it is difficult to select genetic polymorphisms that are associated with certain phenotypes from among such numerous SNPs. In contrast, a gene whose expression level is different between alleles may be correlated with a certain phenotype. Accordingly, the genetic polymorphisms that enable identifying a gene whose expression level is different between alleles searched for by the aforementioned method may more highly be correlated with phenotypes than other types of genetic polymorphisms.

The method for searching for a phenotype-associated genetic polymorphism according to the present invention is characterized in that the genetic polymorphism searched for by the aforementioned method is used to determine the correlation between the genetic polymorphism or gene expression level and the phenotype. Examples of the phenotype include occurrence of a disease (e.g., pathological conditions and severity), risks of developing a disease, responsiveness to drugs, responsiveness to foods, responsiveness to chemical substances, and responsiveness to environmental factors (e.g., ultraviolet rays or temperature).

Specifically, the method of the present invention can be implemented based on the association method, the affected sib-pair method, or the like, known in the art. In the association method, for example, both an analyte that exhibits a certain phenotype and an analyte that does not exhibit a certain phenotype are used to determine the correlation between a frequency of appearance of genetic polymorphisms searched for by the aforementioned method or gene expression level and a phenotype. Where the occurrence frequency of certain genetic polymorphism is significantly high in an analyte exhibiting a certain phenotype, it can be determined that differences in the genetic polymorphism affect quantitative regulation of the expression level of a phenotype-associated gene, or otherwise, changes in the genetic code of a genetic polymorphism, which lead to changes in amino acids and thus to changes in the nature of proteins, such as phenotype expression. In the affected sib-pair method, family members (such as brothers or sisters) having a same phenotype (e.g., a disease) are compared to identify a chromosome region in which a phenotype-associated gene is present. Such a technique is described in, for example, *Sentan no genomu igaku wo shiru* ("Learning the advanced genomic medicine"), Yusuke Nakamura, Yodosha, 2000, Chap. 1.

For example, a gene comprising a genetic polymorphism searched for by the above method exhibits a difference in the expression level of the gene, between alleles, in a same individual. Thus, the expression level is deduced to differ among individuals based on the allele type (i.e., the type of a genetic polymorphism). Measurement of genetic polymorphisms and expression levels of many individuals enables verification of the correlation between expression levels among individuals and genetic polymorphism information.

The method of the present invention enables searching phenotype-associated genetic polymorphisms. A genetic polymorphism searched for in this manner is useful for diagnosing the development of a disease or the risk of developing a disease or for evaluating responsiveness to drugs in advance.

In the present invention, a genetic polymorphism searched for by the above method is used to determine the correlation between the genetic polymorphism or gene expression level and a phenotype. Thus, it becomes possible to search for a phenotype associated with a genetic polymorphism.

Based on the "inherent properties" of a protein encoded by a certain gene (e.g., involvement of PPARγ in lipid metabolism), for example, differences in genetic polymorphism of the gene are deduced to produce different phenotypes. (For example, PPARγ is presumed to be associated with a phenotype involved in the lipid metabolism, such as diabetes.) Accordingly, actual validation of both the genetic polymorphism and the phenotype (e.g., reactivity of an antidiabetic agent, ACTOS™, in various individuals as compared with the results of genetic polymorphism typing of PPARγ) enables verification of the actual involvement thereof.

By using the aforementioned method, we actually discovered that the expression level of human peroxisome proliferator-activated receptor γ (PPARγ or PPARG) genes differs between alleles, and also discovered genetic polymorphisms that would enable determination of differences in genetic expression level between alleles.

EXAMPLES

Hereafter, the method of the present invention will be described in more detail with reference to the following examples; however, it should be understood that the technical scope of the present invention is not limited thereto.

Example 1

In this example, cDNA was synthesized from intranuclear RNA and amplified.

Total RNAs (1 μg each) of lymphoid cell lines, BL1395 (ATCC CRL-5957) and BL2122 (ATCC CRL-5967), established by EB virus, were treated with DNAase and subjected to reverse transcription using reverse transcriptase (Superscript III RT enzyme, Invitrogen) in accordance with the protocol included therein, to prepare single-stranded cDNA. A portion (1 μl) of the resulting 20 μl of reaction solution was added, without purification, to a reaction solution containing a random primer and the phi29 enzyme as described in the protocol of Genomiphi™ (sold by Amersham Bioscience), the reaction was allowed to proceed at 30° C. for 16 hours, and cDNA was obtained (yield: 2.34 μg and 2.27 μg, respectively).

The results of electrophoresis of the thus amplified cDNA are shown in FIG. 1. In FIG. 1, lane 1 and lane 2 show cDNA prepared using phi29 DNA polymerase as described above.

As shown in FIG. 1, a smear from 10 Kb or more to about 3 Kb, centering around about 8 Kb, was obtained (lanes 1 and 2 of FIG. 1). The fact that the median cDNA length was 2,316 bp after synthesis from common mRNA suggests that only long cDNA was selectively amplified. Specifically, it was demonstrated that the use of the phi29 enzyme enabled a selective amplification of cDNA from long-stranded intranuclear RNA.

Example 2

In this example, cDNA obtained from intranuclear RNA in Example 1 was used to perform experiments on SNP typing and gene expression level.

(1) Verification of cDNA Amplification from Intranuclear RNA Using phi29 Enzyme

At the outset, 250 ng of the cDNA amplified in Example I was subjected to a reaction in accordance with the protocol of the 100K array (Affimetrix). Specifically, cDNA amplified with phi29 as described in Example I and genomic DNA similarly amplified with phi29 were amplified in accordance with the protocol of common 100K, the signal intensity ratio (cDNA signal intensity/genomic DNA signal intensity) was determined, and the frequency distribution thereof was then examined. By determining the signal intensity ratio, some sequences are found to be easily amplified with the aid of phi29 and other sequences are found to be less likely to be amplified therewith, depending on differences in secondary structures, which result from differences in sequences (bias of amplification). By dividing the cDNA signal value by the signal value of the genome amplified with phi29, however, such a bias of amplification can be eliminated.

Figure 2:
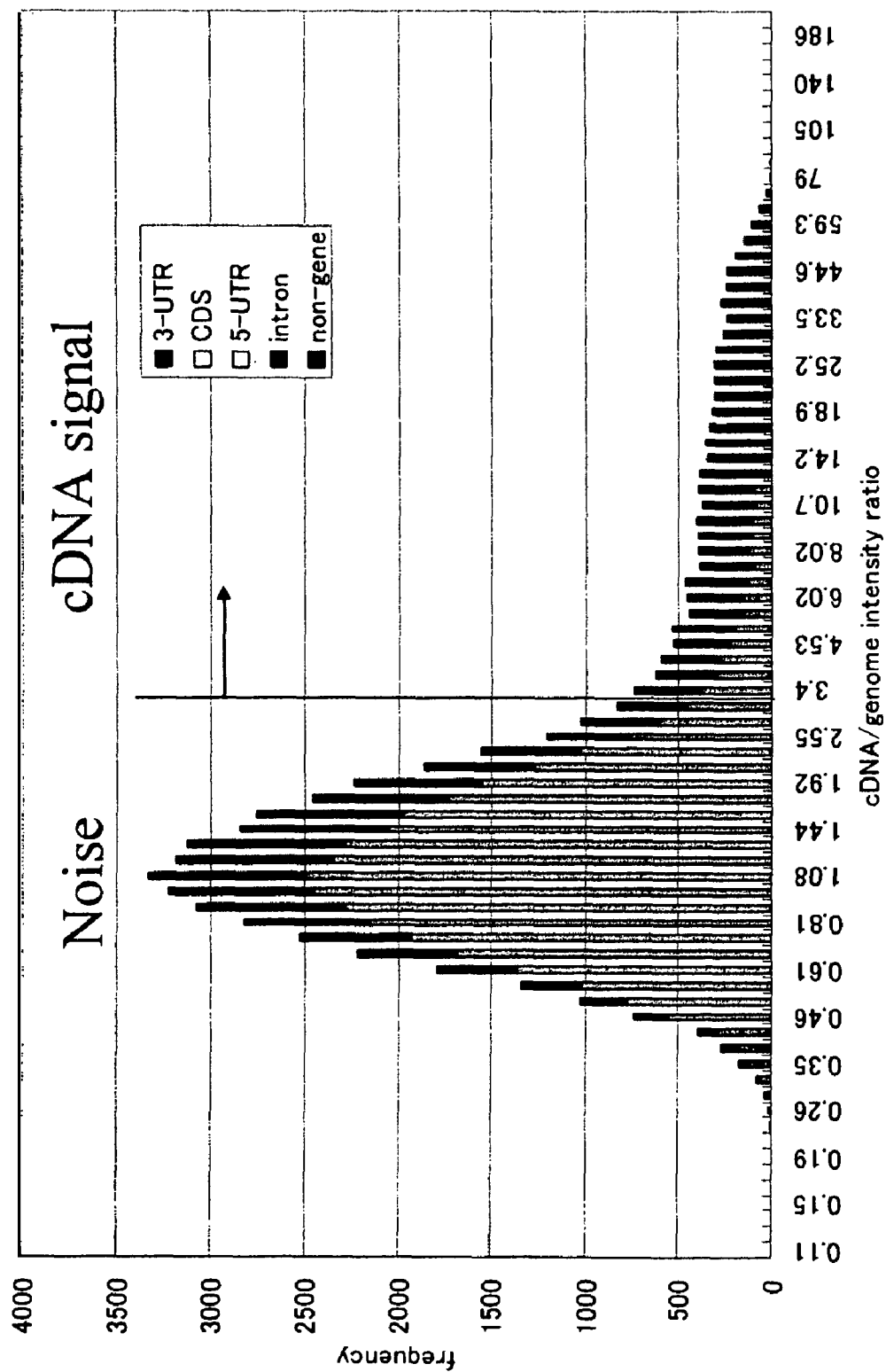
FIG. 2 shows the positional relationship between the frequency distribution of cDNA/genome signal ratios in the lymphocyte BL1395 and the genes on genome in which the genetic polymorphism (the probe set) is present.
Figure 3:
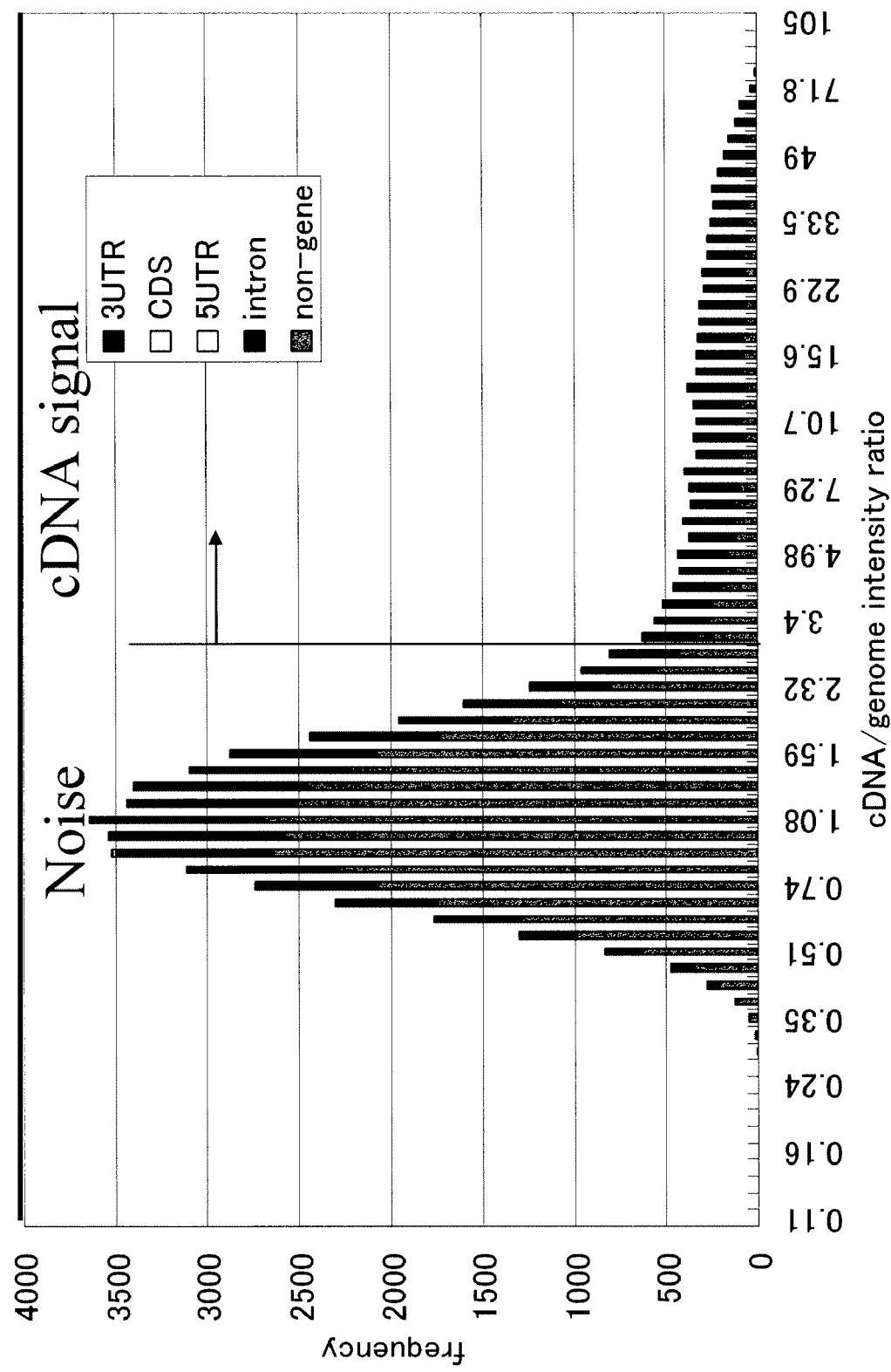
FIG. 3 shows the positional relationship between the frequency distribution of cDNA/genome signal ratios in the lymphocyte BL2122 and genes on the genome in which the genetic polymorphism (the probe set) is present.

As a result, as shown in FIG. 2 and FIG. 3, a shape similar to a normal distribution curve, which appeared to be noises, was observed in regions with low signal ratios, and there were many signals (probe sets) based on the genetic polymorphisms in regions containing no genes (the light gray zone of a bar chart in FIG. 2 and in FIG. 3). In contrast, portions with potent signal ratios were observed in such a manner that the portions are off the aforementioned normal distribution curve, on the right side of FIG. 2 and FIG. 3 (portions indicated with arrows in FIG. 2 and in FIG. 3), and there were many signals (probe sets) based on genetic polymorphisms that were present in regions with genes (substantially regions from the intron). Based on the shape of the frequency distribution and the positional relationship between the probe sets and the gene on genome, it was found that the gene (cDNA)-derived signal was separated from the noises via the assay. By assaying the cDNA signal/genome signal ratio, it was found that portions exhibiting high signal ratios may be considered as representing signals resulting from the expressed gene (primarily cDNA derived from intranuclear RNA).

Also, whether or not the gene expression level assayed with the use of common microarrays is correlated with the cDNA signal/genomic DNA signal ratio analyzed in the above-described manner, was determined using common arrays for expression analysis (Affymetrix U133plus2.0 array; http://www.affymetrix.co.jp/pdf/HG_DS.pdf).

Specifically, total RNA of BL2122 was prepared and analyzed using the Affymetrix U133plus2.0 array in accordance with a common protocol. The entirety was averaged so as to bring the average signal value of about 54,000 probe sets to 100, two groups, a group of genes exhibiting a high signal ratio and a high expression level (a score of 100 or greater) and a group of genes exhibiting a low signal ratio and a low expression level (a score of 10 or smaller), were subjected to determination of a cDNA signal/genome signal ratio from the aforementioned information using probes of SNPs present on the genomic region carrying introns fixed on the 100K array (XbaI 50K used herein), thereby to observe a frequency distribution.

Figure 4:
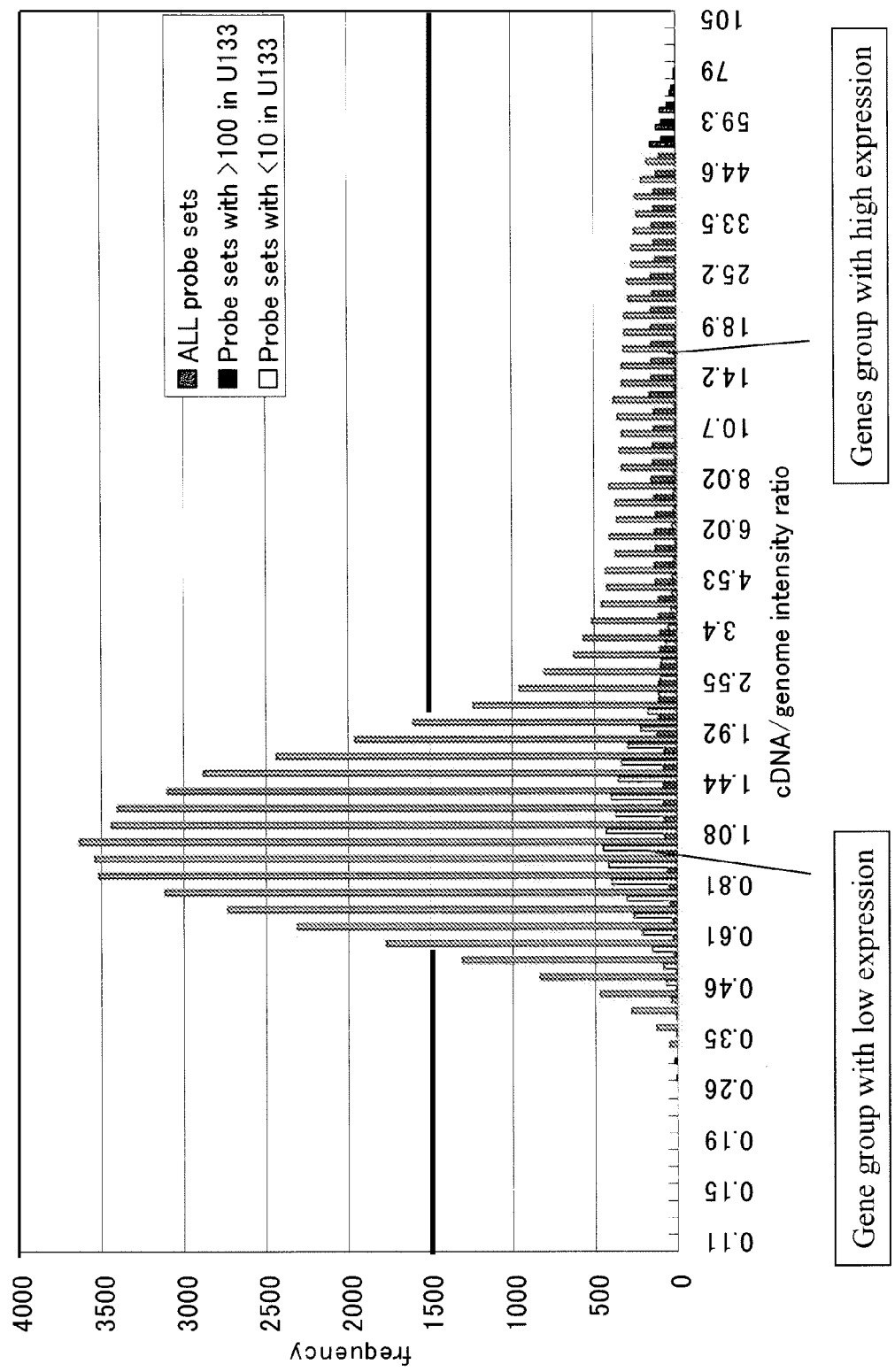
FIG. 4 shows the comparison of cDNA/genome signal ratios determined from U133plus2 array and 100K array (XbaI 50K) for expression analysis.

As a result, as shown in FIG. 4, most genes with low expression level (scores of 10 or smaller with the use of U133plus2.0) were found to be present on the portion, which is considered to be noises as above and exhibits a shape similar to a normal distribution. In contrast, most genes with high expression level (scores of 100 or greater with the use of U133plus2.0) were found to be in the right portion, which is considered to capture signals from cDNA. Accordingly, the cDNA/genome signal ratios determined in this example was correlated with the actual gene expression levels, and long intranuclear RNA comprising introns before being spliced was likely to be more selectively amplified with phi29.

(2) Detection of Difference in Expression Levels Between Alleles

The cDNA/genome signal ratios for two types of alleles (A and B) in BL1395 and BL2122 cell lines (from females) were measured as described in (1) above to determine the RNA (cDNA) levels from allele A and from allele B, and to study differences in expression levels between allele A and allele B, the ratio of the two (i.e., a ratio of the cDNA/genome ratio of allele A to the cDNA/genome ratio of allele B) was determined. Where the ratio is 1:1, the expression levels of the alleles can be equivalent. As a result, statistically significant differences in the expression levels between alleles were observed (i.e., 4.24 and 5.06) in the X chromosome, wherein one allele is well known to be inactivated due to physiological imprinting, as compared with other autosomal chromosomes (1.69 and 2.01), as shown in Table 1.

TABLE 1

|  | Autosomal chromosome | X chromosome | t-test p-value |
|---|---|---|---|
| BL1395 | 1.69 | 4.24 | $1.12 \times 10^{-6}$ |
| BL2122 | 2.01 | 5.06 | $1.70 \times 10^{-8}$ |

Thus, it was demonstrated that the measurement of expression levels of a gene between alleles based on SNPs with the use of 100K array (50K XbaI array) in cDNA, which was amplified with phi29 polymerase, would enable the determination of an expression level for each allele.

Example 3

In this example, differences in expression levels of the PPARG gene between alleles were studied.

Among the genes that had been confirmed to be expressed differentially between alleles in Example 2, PPARG (peroxisome proliferator-activated receptor γ) gene could be selected.

Figure 5:
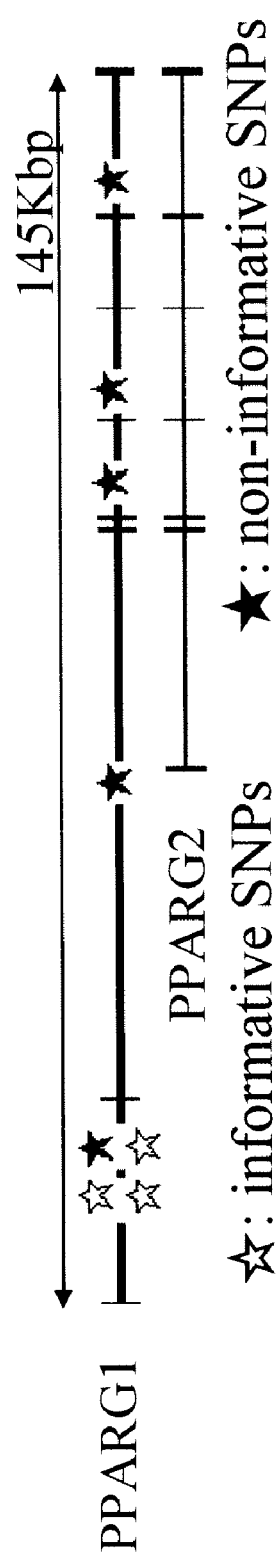
FIG. 5 shows the position of SNP sites on PPARγ gene.

The 50K XbaI array included in the 100K array is designed such that probe sets are comprised at 7 SNP sites in total in the genomic PPARG gene region. When the BL1395 lymphoid cell line was analyzed in Example 2, three SNPs, i.e. rs10510410, rs10510411 and rs10510412 (NCBI dbSNP database IDs), which are closely located within 5'-side 300-bp-region of the PPARG gene, were found to be polymorphisms via genomic typing (i.e., two alleles were distinguishable from each other). FIG. 5 shows the position of these 3 SNPs in the PPARG gene. In FIG. 5, open stars indicate an SNP (i.e., informative SNP) that enables determination of differences in expression levels of the PPARG gene between alleles.

The expression ratio between two alleles (i.e., a ratio of the cDNA/genome ratio of allele A to the cDNA/genome ratio of allele B) was 4 times or higher for any of SNPs, as shown in Table 2.

TABLE 2

| SNP id | Expression ratio between alleles |
|---|---|
| rs10510410 | 4.55 |
| rs10510411 | 4.85 |
| rs10510412 | 6.75 |

Figure 6:
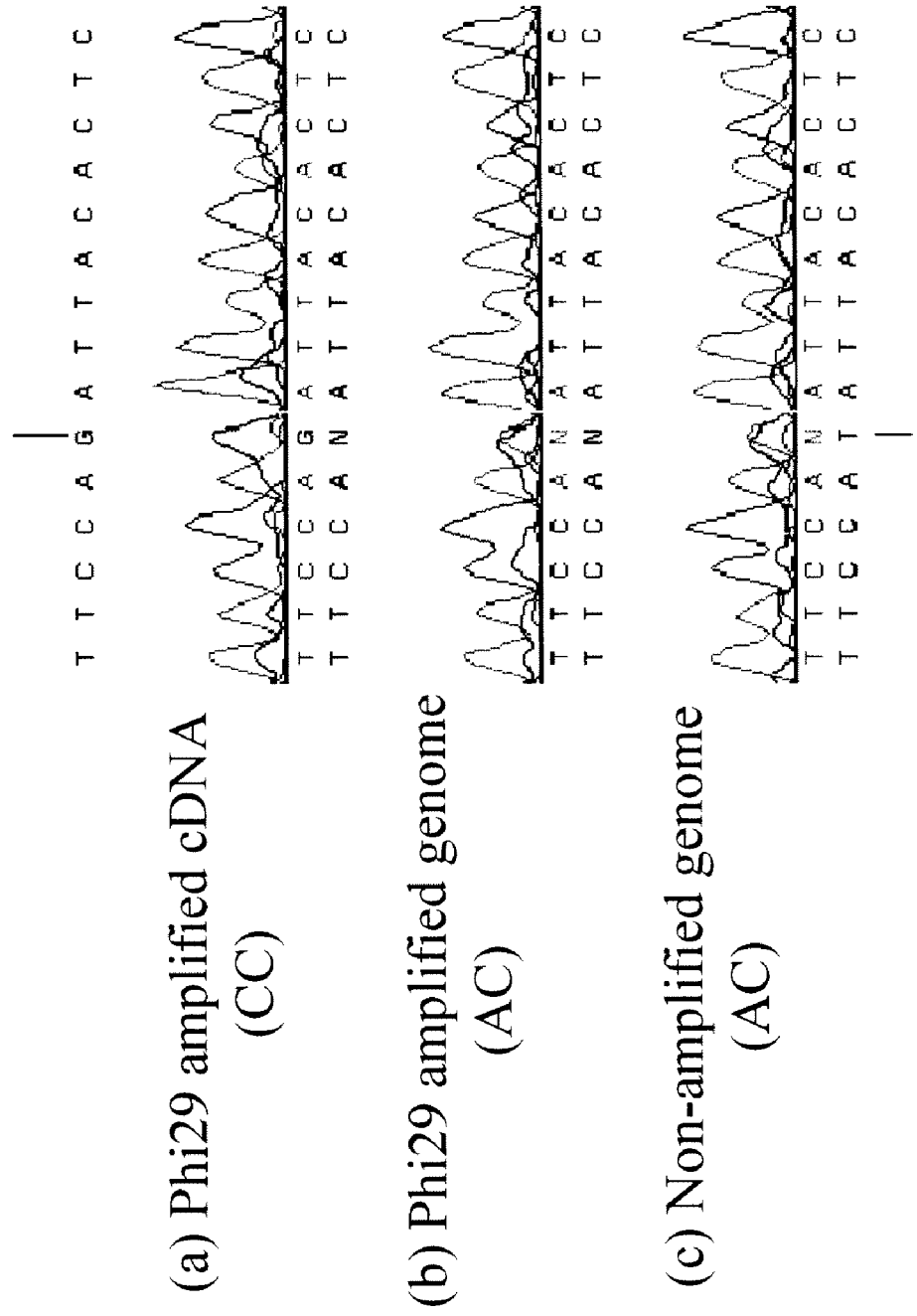
FIG. 6 shows a schematic diagram of identifying SNPs by direct sequencing.

The existing ratio of alleles carrying these 3 SNPs in the region was determined by direct sequencing. The summarized results are shown in FIG. 6. In the case of rs10510410 of the BL1395 sample, for example, A/C heterozygotes were found in genomic DNA (c) as shown in FIG. 6, and there was no change in the genomic DNA amplified with phi29. In the case of cDNAs amplified with phi29 (a and b), the signals from allele A were lowered, and thus a substantial waveform consisting of allele C alone was observed. Specifically, rs10510410 is an A/C heterozygote on the genome; however, the expression level of the gene that is actually expressed from allele C was found to be high. This result was consistent with the result obtained using 50K XbaI array. Expression of the PPARG gene was not observed in BL2122 lymphoid cell line.

Thirty Japanese individuals were subjected to typing via direct sequencing to study the correlation between these 3 SNPs and the expression of the PPARG gene of peripheral blood lymphocytes. Specifically, the correlation between the 3 SNP types and the expression levels of the PPARG gene was analyzed. The expression analysis of the PPARG gene was carried out using the CodeLink, which is the array for expression analysis (Amersham Bioscience), in accordance with a common protocol thereof, and the signals of all probes for each array were averaged so as to bring the median to 1.

Figure 7:
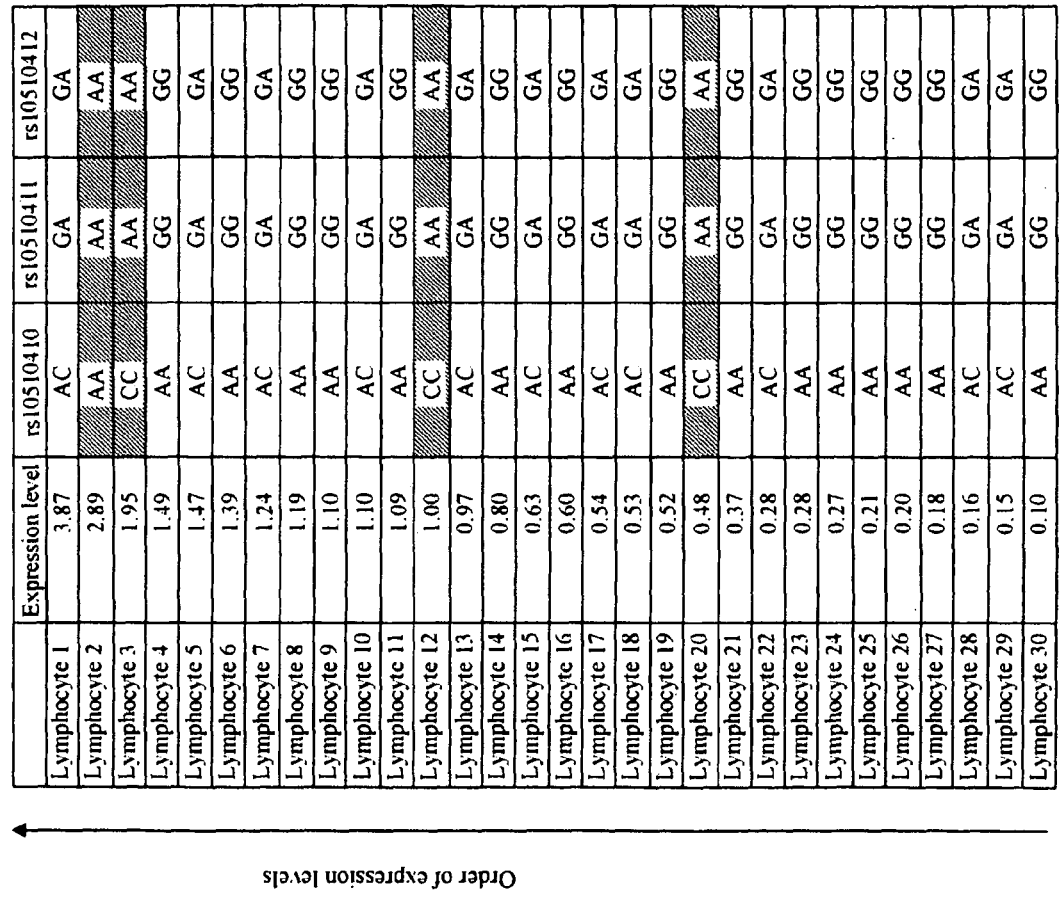
FIG. 7 shows the correlation between the expression level of the PPARG gene of peripheral blood lymphocytes obtained from 30 Japanese individuals and the typing of genetic polymorphisms.
Figure 8:
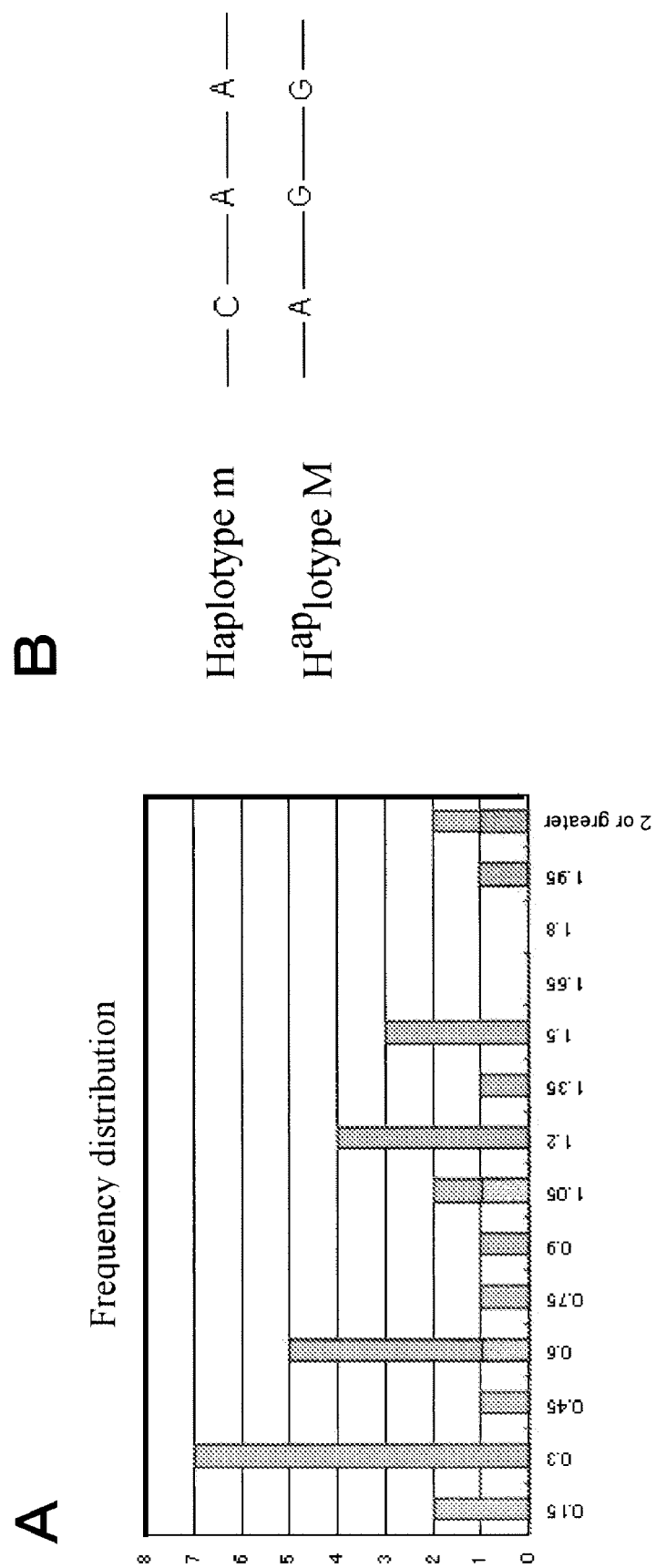
FIG. 8 shows the frequency distribution of the expression levels and genetic polymorphism typing of the PPARG gene in peripheral blood lymphocytes obtained from 30 Japanese individuals (FIG. 8A), and alleles of haplotype M and haplotype m (FIG. 8B).

Consequently, as shown in FIG. 7 and FIG. 8A (tables and frequency distribution), specimens were classified in accordance with the existence frequency in 30 Japanese individuals as follows: C, A, and A homozygotes of alleles (m) with a low abundance frequency in rs10510410, rs10510411, and rs10510412; A, G, and G homozygotes of alleles (M) with a high existence frequency in rs10510410, rs10510411, and rs10510412; and heterozygotes thereof. In the case of homozygotes of alleles with a low abundance frequency (mm homozygotes, shaded in FIG. 7 and in FIG. 8A), the expression level was higher than in the cases of other types of homozygotes (i.e., mM and MM homozygotes) (the average of mm: 1.58; the average of others: 0.80). Among the 3 top specimens exhibiting the highest expression levels, 2 specimens were of the mm type.

Thus, the presence of such SNPs (haplotypes) was found to be correlated with the expression level of the PPARG gene, and the SNP typing was suggested to be effective for determining individual PPARG activity, diagnosing and screening for diseases that may be associated with PPARG, and determining responsiveness to a drug that targets PPARG.

In the specimens from 30 individuals, the combination of major allele M with minor allele m was completely consistent in 3 SNP sites (rs10510410, rs10510411, and rs10510412) (FIG. 7). Thus, the 3 SNPs were in complete linkage disequilibrium and formed haplotypes. As shown in FIG. 8B, two haplotypes M and m are present, and haplotype m exhibited a higher expression level of PPARG (FIG. 7). By determining SNPs in the haplotypes or in the vicinity thereof that is in linkage disequilibrium, the aforementioned object was considered to be attained.

A genetic polymorphism that enables determination of a gene whose expression level is different between alleles and that is searched for by the method of the present invention, is suggested to be correlated with gene expression level and to influence phenotype.

All publications, patents, and patent applications cited herein are incorporated herein by reference in their entirety.

INDUSTRIAL APPLICABILITY

The present invention provides a method for rapidly and effectively searching for a genetic polymorphism that enables determination of a gene whose expression level is different between alleles. The thus-searched for genetic polymorphism enables distinguishing expression levels between alleles. Accordingly, such a genetic polymorphism can be an effective means for analyzing a phenotype associated with a gene of interest. Further, if the correlation between the thus searched genetic polymorphism and a phenotype (e.g., a risk of developing a disease or drug responsiveness) is found, then its finding will be utilizable for studying a cause of a disease or effective therapeutic methods.

SEQUENCE LISTING FREE TEXT

SEQ ID NOs.: 1 to 3: partial sequences of human peroxisome proliferator-activated receptors γ ("n" represents g or t in SEQ ID NO: 3).

The invention claimed is:

1. A method for searching for a genetic polymorphism, which genetic polymorphism is capable of identifying a gene the expression level of which differs between alleles of said gene, comprising the steps of:
    (a) selectively amplifying cDNAs derived from about 3 kb or more intranuclear RNAs among cDNAs derived from RNAs of a biological sample, using random primers and phi29 DNA polymerase;
    (b) detecting genetic polymorphisms in the amplified cDNAs;
    (c) comparing expression levels of RNAs from the respective alleles, using the amplified cDNAs, at each of the detected polymorphisms; and
    (d) selecting among said detected polymorphisms to identify at least one polymorphism that is characterized by significantly different expression levels between alleles thereof.

2. The method according to claim 1, wherein steps (b) and (c) comprise labeling the amplified cDNAs, which are in turn subjected to hybridization with a genetic polymorphism-specific probe, to compare the expression levels of cDNAs from respective alleles based on the hybridization reaction.

3. The method according to claim 1, wherein the genetic polymorphism is a single nucleotide polymorphism.

4. A method for searching for a phenotype-associated genetic polymorphism, comprising establishing a correlation between a phenotype and a polymorphism identified by the method of claim 1.

5. The method according to claim 4, wherein the phenotype is selected from the group consisting of pathological conditions and severity of a disease, risks of developing a disease, responsiveness to drugs, responsiveness to foods, responsiveness to chemical substances, and responsiveness to environmental factors.

6. The method according to claim 2, wherein said cDNA is hybridized to at least two probes separately, wherein each of said probes is specific for a different allele of a genetic polymorphism, such that the presence of said polymorphism in said cDNA results in a signal associated with each probe.

7. A method for searching for a phenotype associated with a genetic polymorphism, comprising using a genetic polymorphism identified by the method according to claim 1 to evaluate a correlation between the genetic polymorphism and the phenotype.

* * * * *

UNITED STATES PATENT AND TRADEMARK OFFICE
CERTIFICATE OF CORRECTION

| | | |
|---|---|---|
| PATENT NO. | : 7,794,982 B2 | Page 1 of 1 |
| APPLICATION NO. | : 11/721737 | |
| DATED | : September 14, 2010 | |
| INVENTOR(S) | : Hiroyuki Aburatani and Shumpei Ishikawa | |

It is certified that error appears in the above-identified patent and that said Letters Patent is hereby corrected as shown below:

<u>ON THE TITLE PAGE</u>

Please correct the following:

Item (73) Assignee: Please change "The University of Tokyo, Tokyo (JP)" to -- The University of Tokyo, Tokyo, (JP) and Haplopharma Inc., Tokushima (JP) --.

Signed and Sealed this
Fifteenth Day of March, 2011

David J. Kappos
*Director of the United States Patent and Trademark Office*